United States Patent [19]

Joseph et al.

[11] Patent Number: 4,602,502

[45] Date of Patent: Jul. 29, 1986

[54] WAVE SPEED METER

[75] Inventors: Daniel D. Joseph; Oliver Riccius, both of Minneapolis, Minn.

[73] Assignee: Regents of the University of Minnesota, Minneapolis, Minn.

[21] Appl. No.: 693,210

[22] Filed: Jan. 22, 1985

[51] Int. Cl.[4] ............................................. G01N 11/00
[52] U.S. Cl. .......................................... 73/60; 356/427
[58] Field of Search ............................. 73/60; 356/427

[56] References Cited

PUBLICATIONS

Lieb, Eugene Bach., *Viscoelastic Flow Behavior in Accelerating Shear Fields*, University of Rochester, Rochester, NY, 1975.

Narain, A. and D. D. Joseph, *Linearized Dynamics for Step Jumps of Velocity in Displacement of Shearing Flows of a Simple Fluid*, Rheologica, 21, pp. 228–250.

Narian, A. and D. D. Joseph, *Remarks about the Interpretation of Impulse Experiments in Shear Flows of Viscoelastic Liquids*, Rheologica Acta, pp. 528–538.

*Primary Examiner*—Stewart J. Levy
*Assistant Examiner*—Joseph W. Roskos

*Attorney, Agent, or Firm*—Kinney & Lange

[57] ABSTRACT

A wave speed meter comprises a pair of relatively rotatable, concentric cylinders with a gap between the cylinders to define a chamber. A viscoelastic fluid is placed in the chamber, and one of the cylinders is suddenly rotationally displaced causing a shear induced wave to be propagated through the fluid filling the chamber between the cylinders. This wave is propagated toward the other cylinder and when the wave reaches the other cylinder the other cylinder moves. The transit time of the wave is determined by measuring the time between the displacement of the one cylinder and movement of the other cylinder as a result of the wave. The distance that the wave travels is known, so that the wave speed can be determined. In the form shown a counter is initiated at the time the one cylinder is displaced, and then disabled at the time when the other cylinder moves, using electro-optical techniques that are simple to utilize because mirrors can be mounted on the two cylinders and the motion of the cylinders can be amplified by properly locating the sensors that sense the beams reflected by the mirrors.

17 Claims, 4 Drawing Figures

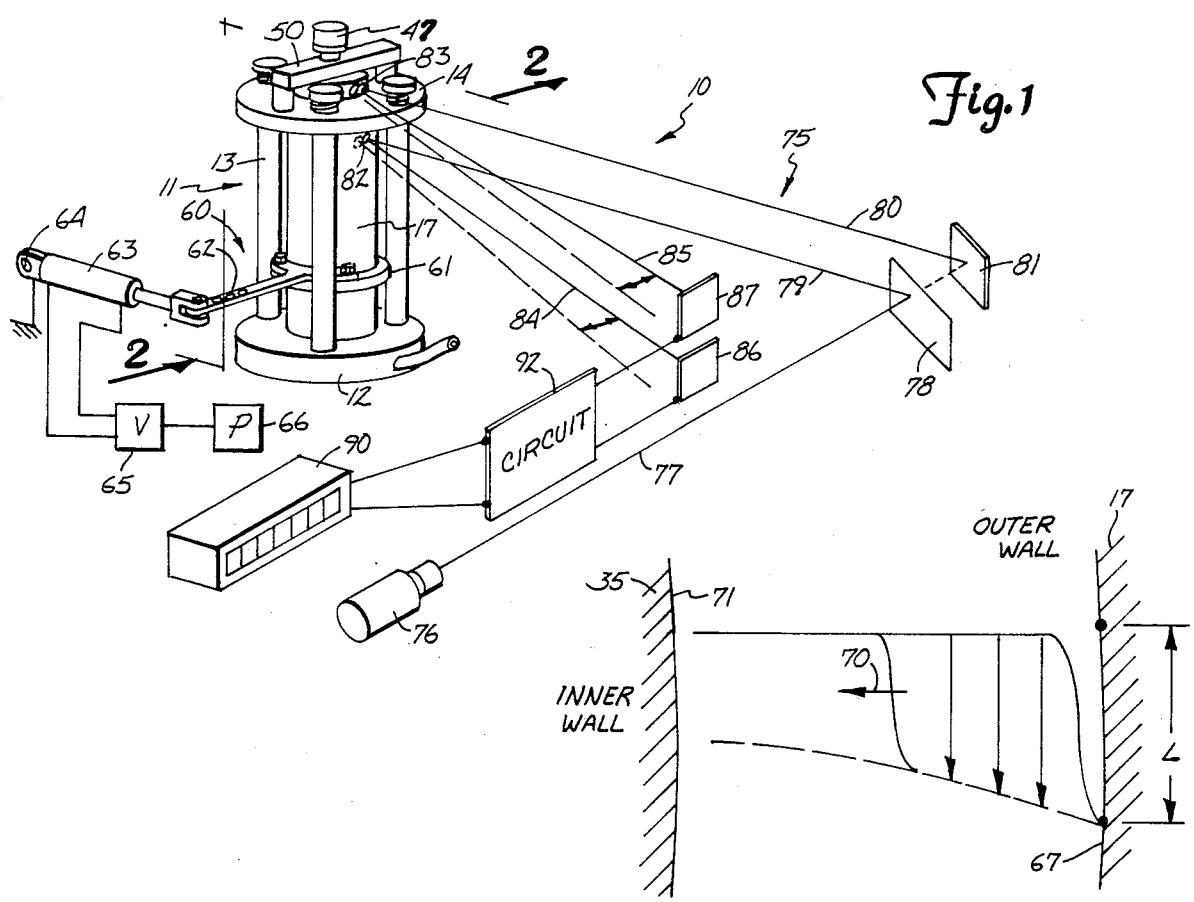
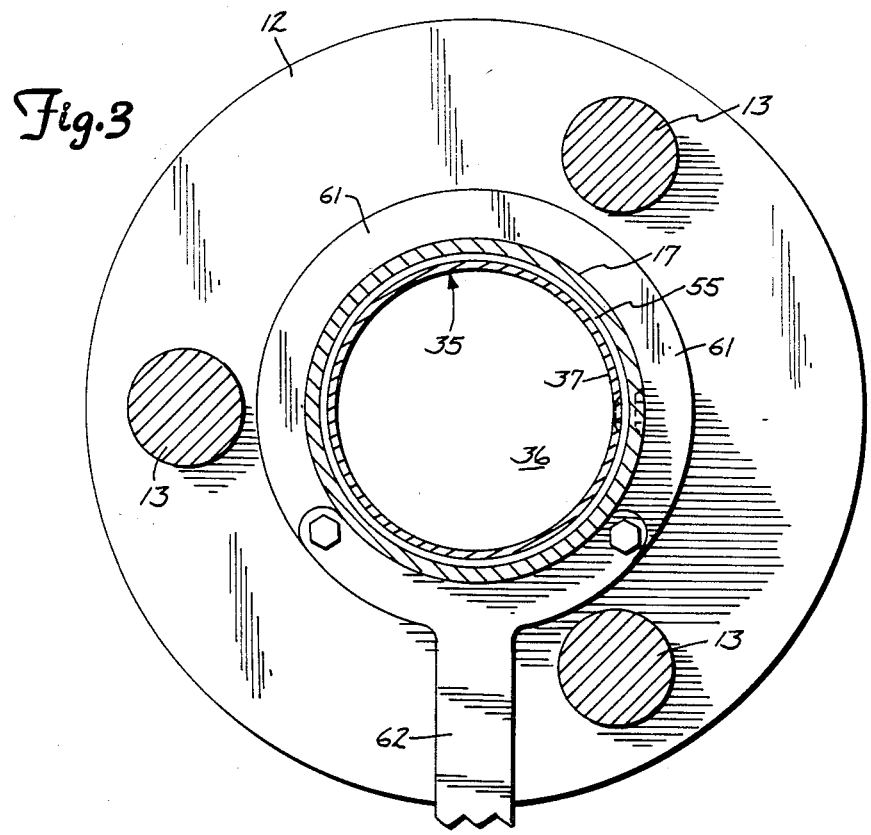

WAVE SPEED METER

This invention was made with Government support under DAAG Contract #29-82-K-0051 awarded by the Department of the Army. The Government has certain rights in this invention.

BACKGROUND OF THE INVENTION

1. Field of the Invention

The present invention relates to a wave speed meter for determining the propagation speed of a shear induced wave in a viscoelastic fluid.

2. Description of the Prior Art

Viscoelastic fluids such as polymer solutions and melts of polymers (molten plastic), can support the propagation of various kinds of waves of shear; in such fluids an event which takes place in one place in the fluid will take a certain time to reach another place. These wave speeds are a fundamental property of elastic fluids, but no instruments exist for directly measuring the wave speeds.

The propagation of shear induced waves through viscoelastic fluids has been discussed in a thesis prepared by Eugene Bach Lieb, at the University of Rochester, Rochester, N.Y., 1975, entitled "Viscoelastic Flow Behavior In Accelerating Shear Fields." Measurement of wave speed was made utilizing photographic techniques which illustrated traveling shear waves across a gap in a rheometer.

In an article entitled "Linearized Dynamics For Step Jumps Of Velocity In Displacement Of Shearing Flows Of A Simple Fluid," *Rheologica Acta,* 21, pp. 228–250, 1982, A . Narain and D. D. Joseph (one of the present inventors) showed that the propagation speed of small amplitude waves of slip lines of velocity and displacement is given by $$C = \sqrt{G(0)/\rho}$$

where $\rho$ is the density of the fluid and $G(0)$ is the instantaneous value of the shear relaxation modulus of the fluid or liquid that is being tested. There are some methods currently available to measure the relaxation function $G(s)$ of some liquids, but these methods are not accurate for small values of the lapsed time s. By measuring the wave speed "C", the instantaneous value $G(0)$ of the relaxation function $G(s)$ can be determined.

An additional reference to descriptions of the relaxation function $G(s)$ includes the article entitled "Remarks About The Interpretation Of Impulse Experiments In Shear Flows Of Viscoelastic Liquids," A. Narain and D. D. Joseph, *Rheologica Acta,* 22, pp. 528–538, 1983.

SUMMARY OF THE INVENTION

The present invention relates to an apparatus and method for determining the propagation speed of small amplitude waves in viscoelastic liquids.

In the apparatus, an amount of the test viscoelastic liquid is placed in a chamber defined by two relatively movable, facing surfaces that are independently supported with a known length gap between the surfaces. The surfaces are preferably left at rest. One of the surfaces is then displaced with a sudden velocity, and because the liquid carries shear, a shear wave is formed at the boundary layer of the liquid at the one surface by this sudden displacement of that surface.

The wave travels across the gap and when it reaches the independently supported second surface, the second surface is shifted or moved because of shear forces acting on the boundary layer of the second surface. The time when the movement of the second surface occurs is measured relative to the initial displacement of the first surface. The wave transit time thus can easily be determined. The wave speed can be calculated from the transit time and the distance travelled (the distance between the two surfaces).

In the form shown, concentric cylinders are utilized with facing spaced surfaces defining a chamber holding an annular band of viscoelastic liquid. A sudden acceleration is imparted to one of the cylinders for rotation about its central axis, and when the wave caused by shear at the first cylinder surface reaches the second cylinder, the second cylinder is caused to rotate. The time at which the rotation of the second cylinder occurs can be measured so that the elapsed time can be accurately determined.

In the preferred embodiment shown, the time of displacement of the first cylinder and the time of displacement of the second cylinder caused by the propagated wave reaching the second cylinder are determined by electro-optical means comprising mirrors on each of the cylinders which reflect beams onto photosensitive members, so that when the first cylinder is shifted the beam reflected by the respective mirror moves off the associated photosensitive member causing a counter to start, and when the shear wave in the liquid reaches the second cylinder, the second cylinder shifts sufficiently so that the beam reflected by the mirror on the second cylinder moves away from its photosensitive member to disable the counter.

By using a laser source and a beam splitter for the beams a simple and accurate determination of elapsed travel time of the wave between the surfaces is made.

As shown, the cylinders are mounted on bearings on a common base, but independently rotatable, and the bearings provide some damping for the cylinders. The amount of damping can be adjusted by preloading the bearings a desired amount. In the form shown the outer cylinder is displaced by operating a pneumatic actuator that suddenly displaces the outer cylinder a known amount to give a relatively high acceleration to the boundary layer liquid, which causes a clearly discernable shear wave to be formed and propagated through the fluid to the second cylinder.

Various forms of determining elapsed time can be used, and also various configurations of members having surfaces that are independently movable can be utilized for providing the chamber for containing the test liquid.

The cylindrical form is advantageous in that cylinders provide large surface areas in a relatively small space, thereby insuring that the propagated wave will provide an impulse to the inner cylinder when it reaches the inner cylinder that will cause a reliable movement of the inner cylinder.

BRIEF DESCRIPTION OF THE DRAWINGS

FIG. 1 is a perspective view of a preferred form of the present apparatus used for determining wave speed propagation according to the present invention;

FIG. 3 is a sectional view taken as on line 3—3 in FIG. 2; and

FIG. 4 is a part schematic representation of the apparatus of the present invention schematically illustrating a typical shear wave.

DETAILED DESCRIPTION OF THE PREFERRED EMBODIMENTS

Figure 2:
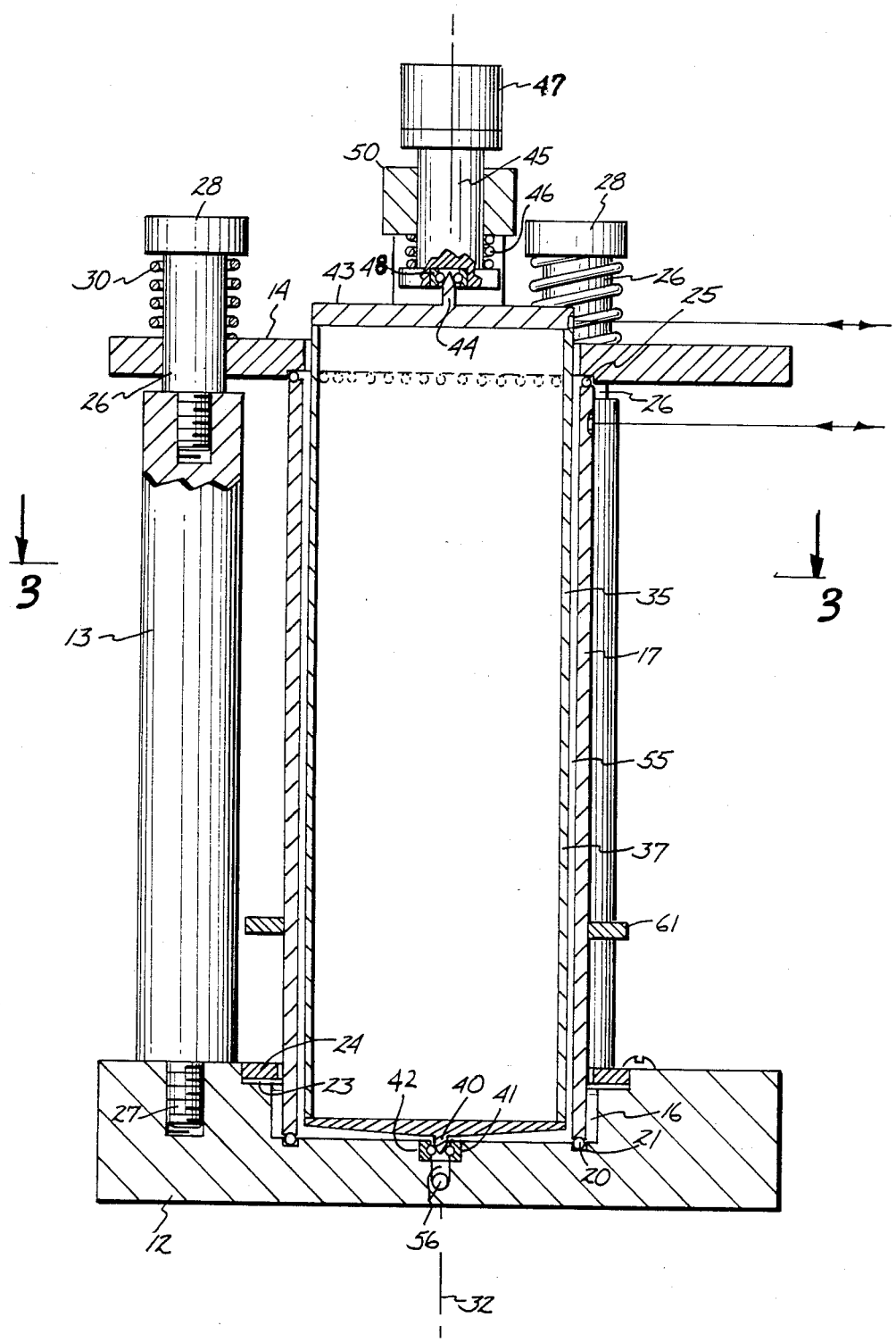
FIG. 2 is an enlarged vertical sectional view taken on line 2—2 in FIG. 1.

An apparatus for measuring wave speeds of viscoelastic fluids (liquids) is shown generally at 10. The test liquids support propagation of waves of shear. The apparatus comprises a frame assembly 11, including a base 12, a plurality of upright columns 13 and an upper retainer plate 14. The base 12, as shown in FIG. 2, has an interior cylindrical receptacle 16 in the center portions thereof, which closely receives a tubular cylinder 17 for rotation. The tubular cylinder 17 is supported on suitable ball bearings 20, placed in a groove 21 at the periphery of the central receptacle 16, so that the end surface of the wall forming the tubular cylinder 17 is supported on the base. A suitable low friction teflon seal 23 is used adjacent to the outer surfaces of the tubular cylinder 17 so that it is rotatably sealed relative to the surfaces defining the receptacle 16. The seal 23 is held in place by a retainer 24.

The upper retainer plate 14 as shown has a central opening therethrough, and an annular shoulder or recess indicated at 25 around this opening has suitable balls 26 that align with the upper end surface of the tubular cylinder 17. The retainer plate 14 is held on the posts or columns 13 through the use of shoulder bolts 26 that thread into the upper ends of the columns, and as shown the lower ends of the columns are threaded as at 27 into the base 12. The shoulder bolts 26 have heads 28 that retain suitable springs 30 which bear against the upper surface of the retainer plate 14 so that the retainer plate holds the balls 26 against the upper end of the tubular cylinder 17, and the cylinder 17 is thus preloaded with a desired amount of force against the balls 20. However, the outer tubular cylinder 17 easily rotates, and is mechanically displaced or rotated as will be described.

The tubular cylinder 17 forms a first movable member that is movable in rotational directions about its central longitudinal axis, which is generally indicated at 32.

A second or inner movable cylinder or member 35 is mounted on the interior of the tubular cylinder 17, and is concentric therewith. That is, the central axis of the second cylinder 35 is also the axis 32. The tubular cylinder 17 is open at its ends and the cylinder 35 is independently rotatably supported. Cylinder 35 may be a solid cylinder, but as shown an inner end wall 36 is sealed to the outer wall 37 of the cylinder 35 and this inner end wall 36 is provided with a suitable centering cone point 40 that rests on a suitable sealed ball bearing 41 that is held in a suitable bearing seat 42 defined in the base 12 at the center of the receptacle 16.

The upper end of the inner cylinder 35 has a cover plate 43 mounted thereon, and this cover plate is provided with a centering cone point 44 that bears against another suitable sealed ball bearing 48, seated in a support 45, and identical to bearing 41. The bearing support 45 is suitably biased in downward direction with a spring 46 to provide a load against the bearings supporting the second cylinder 35. As shown, a weight indicated at 47 also can be provided on the top of the bearing support 45. The bearing support 45 is slidably mounted in a bridge strap 50, which in turn is supported on the retainer plate 14 at its opposite ends, as shown in FIG. 1. The bridge strap 50 can be held with suitable support blocks 51, as shown.

Thus, each of the cylinders 17 and 35 is independently rotatably supported for movement about the central axis 32 and both cylinders have circular cross sections.

As can be seen, the receptacle 16, the end cap 36, the wall 37 of the cylinder 35, and the inner surfaces of tubular cylinder 17 define an annular chamber 55 that surrounds the inner cylinder 35. Chamber 55 is filled with a viscoelastic liquid which is to be tested for determining the speed of propagation of shear waves through the liquid. The liquid is filled in through a passageway 56 in the base 12 that feeds through the bearing 41 to fill the chamber 55 to a desired level, which is less than the height of the outer tubular cylinder 17.

The tubular cylinder 17 is then rotationally displaced, or imparted with a velocity from rest, through the use of a drive mechanism shown generally at 60 in FIG. 1. A ring 61 is clamped to the outer surface of the tubular cylinder 17 in a desired manner, and a lever arm 62 is mounted on the ring 61 and extends out between two of the columns 13 as shown in FIG. 1. A pneumatic cylinder or actuator 63 has its rod connected to the arm 62 at a desired location. The base of the actuator 63 is mounted onto a suitable support 64 of conventional design that is attached to a table or support on which the mechanism 10 is mounted.

When fluid under pressure is admitted into the actuator 63 quickly, through the use of a valve 65, from a pressure source 66, the rod will retract (or extend if desired) rapidly, moving the lever 62 a desired displacement or distance at a desired velocity. The ring 61 rotates the tubular cylinder 17 about the axis 32 a desired amount. Each particle of the boundary layer of liquid particles on the inner surface of the tubular cylinder 17, will be moved a distance (L) as shown in FIG. 4. The tubular cylinder 17 is subjected to relatively rapid movement, and the inner surface 67 of the tubular cylinder 17 will transmit the motion to the liquid as a wave due to shear in the particles of the visoelastic liquid filling the chamber 55. The resultant wave will be propagated in direction as indicated by the arrow 70 in FIG. 4 toward the surface 71 of the inner cylinder 35.

The wave propagates across the gap width or radial dimension of the chamber 55 at a speed dependent on the relaxation function of the liquid. While the wave decreases in amplitude as it travels this distance, generally as shown in FIG. 4, when the wave reaches the boundary layer on the surface 71 (which is at rest, as shown) it will impart, through shear in the liquid, a force that will tend to rotate the inner cylinder 35 and cause the surface 71 to move the same direction as the direction of displacement L of the tubular cylinder 17. The force from the wave will cause the inner cylinder 35 to rotate on its bearings because it is independently supported relative to the outer tubular cylinder 17.

An apparatus for determining the elapsed time between the initial displacement of the cylinder 17 and the movement of the inner cylinder 35 imparted with motion when the wave reaches it includes time measurement apparatus shown generally at 75. In this form of the invention, a laser beam source 76 provides a laser beam represented at 77 through a conventional beam splitter 78, that reflects one beam 79 from the beam splitter 78, and a second beam 80 is reflected from a mirror 81 toward the apparatus 10. As shown in FIG. 1, the first or outer cylinder 17 has a first mirror 82 on the outer surface thereof suitably located so that the beam 79 will strike it, and the inner cylinder 35 has a second mirror 83 on its outer surface generally aligned in axial direction with the mirror 82 at rest position.

The mirrors 82 and 83 reflect beams 84 and 85, respectively, back to individual photosensitive sensors indicated at 86 for receiving the beam 84, and at 87 for receiving the beam 85.

While shown only schematically, these photosensitive sensors generally comprise photosensitive transistors or other solid state components that are connected into a circuit 92 which is used to control a suitable counter indicated at 90. While the particular details of the circuit 92 are not illustrated, the interconnection of the photosensitive sensors 86 and 87 is conventional in the art.

When the rod of the actuator 63 is retracted, the tubular cylinder 17 is rotated (displaced) through an angle, thus shifting mirror 82 so the reflected beam 84 changes in angle to its dotted line position in FIG. 1, so that the reflected beam 84 no longer strikes the photosensitive sensor 86. When the beam 84 shifts from the sensor 86 the circuit 92 will energize or start the counter 90, which will count up or count down as desired. At the time that the inner cylinder 35 is moved because of the propagated wave striking the cylinder to cause movement, as previously explained the cylinder 35 will rotate through a second angle in the same direction as the rotation of the tubular cylinder 17, and mirror 83 will change in angle and will cause the reflected beam 85 to move to its dotted line position as shown in FIG. 1 where it no longer will contact the photosensitive sensor 87. Sensor 87 is connected through circuit 92 to the counter 90, and will disable the counter 90 and stop the count when the reflected beam 85 no longer contacts it. It should be noted that if the cylinders 17 and 35 shift so that beams 79 and 80 no longer strike the mirrors on the cylinders the same effect is achieved, in that no reflected beams will then strike the photosensitive sensors.

The elapsed time between the time when the beam 84 shifts to its dotted line position until the time when the beam 85 shifts to its dotted line position can accurately be determined by the counter 90.

The elapsed time can be measured in many different ways and the specific way of measuring this time is not critical to the invention. There are two separate movements, the first actuator induced movement is sensed for commencing the timing period and the second wave induced movement is sensed for ending the timing period, to determine the elapsed time for travel of the shear induced wave across the distance or gap of the chamber 55 from one surface of one cylindrical member to the corresponding surface of the other cylindrical member.

The method of determining wave speed comprises providing a chamber for containing the viscoelastic fluid between two spaced, independently supported and movable surfaces which are preferably, although not necessarily, at rest. An acceleration, velocity or displacement (a sudden rapid displacement gives both velocity and acceleration) is imparted to one of the surfaces, and because the viscoelastic fluid shears, a shear induced wave is indicated adjacent the displaced surface and is propagated through the viscoelastic fluid or liquid, until the wave reaches the second surface, at which time a shear induced force moves the second surface. The elapsed time of travel of the wave is measured by any desired device. The reflected beams as disclosed specifically are convenient to use, and very accurate. The distance between the surfaces is known and thus wave speed can be determined.

Additionally, once the wave speed is known, by determining the transit time and the distance traveled, the instantaneous value of the relaxation function for the liquid can be determined accurately and conveniently. This important rheometrical data is unattainable in the standard practices of the prior art devices.

While shown specifically in a form where both the members defining the surfaces which are sensed for movement commence at rest, if proper instrumentation is made, the members could be both moving when an acceleration is imparted to one of the members to shift one member relative to the other sufficiently to create a wave that propagates across the space filled with fluid. The sensing of the time when the wave reaches the second member is possible, with rotational velocity sensors, but the instrumentation and control is more complex.

Also, the outer cylinder could be rotating at a desired constant angular velocity relative to the inner cylinder, with the inner cylinder held at rest by a suitable restraint, such as a torsion wire which resists small torques. In such arrangement, the outer cylinder is then accelerated or pulsed to create a wave, and the time when the effect of the wave reaches the inner cylnder is determined. When the wave reaches the inner cylinder it causes a shift of the inner cylinder which can be sensed with suitable instruments.

Although the present invention has been described with reference to preferred embodiments, workers skilled in the art will recognize that changes may be made in form and detail without departing from the spirit and scope of the invention.

We claim:

1. Apparatus for measuring the speed of propagation of waves in a viscoelastic fluid comprising:
   a first movable member, said first movable member having a first surface and being movable in a first direction;
   a second movable member having a second surface spaced from said surface of said first movable member in a desired orientation relative thereto, and being mounted for movement in said first direction independent of said first member;
   containment means associated with said first and second surfaces for containing a viscoelastic fluid in a space between the surfaces, said second movable member being movable independently of said first movable member;
   means for displacing said first movable member in said first direction at a selected velocity and distance relative to said second movable member sufficient to induce a wave in said fluid; and
   means for determining the time differential from displacement of said first movable member by said means for displacing until said second movable member is displaced in said first direction when a wave in the fluid initiated by displacing the first movable member reaches said second movable member.

2. The apparatus as specified in claim 1 wherein said first movable member surrounds a portion of said second movable member, and said second movable member is supported for movement in said first direction independently of said first movable member.

3. The apparatus as specified in claim 1 wherein said first movable member comprises a tube having a central axis, said second movable member being concentric with said first movable member, and said first direction being a rotational direction about said central axis.

4. The apparatus as specified in claim 3 wherein said containment means comprises a base at an end of said tube and said concentric second movable member, said second movable member being rotatably supported on said base.

5. The apparatus as specified in claim 4 wherein said first movable member is rotatably supported on said base independently of said second movable member, and means defining a passageway in said base for introduction of a viscoelastic fluid to be tested into the space between said first and second movable members.

6. The apparatus as specified in claim 1 wherein said means for determining the time that the said first movable member is displaced comprises means for starting a counter when said first movable member is displaced.

7. The apparatus as specified in claim 6 and means to sense rotational motion of said second movable member to disable said counter when the wave initiated by displacement of said first movable member has been propagated to said second movable member.

8. The apparatus as specified in claim 7 wherein said means for starting a counter comprises a first mirror mounted on said first movable member, means providing a light beam reflected by said first mirror, a first photosensitive element associated with said counter, said first photosensitive element being operable to initiate said counter when the reflected beam moves relative to said first photosensitive element, said means for determining when the wave in the viscoelastic fluid reaches the second movable member comprising a second mirror on said second movable member, means for providing a light beam on said second mirror and a second photosensitive element for receiving the beam reflected from said second mirror, said second photosensitive element being operable to disable said counter when the beam reflected from said second mirror moves relative to said second photosensitive element.

9. An apparatus for measuring the wave speeds in viscoelastic liquids comprising first and second concentric circular cylinders, said first cylinder having an inner surface surrounding said second cylinder, and said second cylinder having an outer surface spaced a desired distance from said first surface to form a substantially annular chamber;
   means to rotatably mount said first and second cylinders independently of each other about the same axis;
   means for closing at least first ends of said first and second cylinders to close said annular chamber between said cylinders to render the chamber capable of holding a viscoelastic liquid to be tested;
   a quantity of viscoelastic liquid filling in said chamber;
   means to impart a sudden change in rotational displacement to one of said cylinders relative to the other to create a wave in the viscoelastic liquid; and
   means to determine an elapsed time which is between the initiation of the sudden change in rotational displacement of said one cylinder relative to the other and the movement of the other cylinder when the wave caused by the sudden change of rotational displacement of said one cylinder reaches the other cylinder.

10. The apparatus as specified in claim 9 wherein said means for determining the elapsed time includes means for detecting the time of arrival of the wave at the other cylinder caused by movement of the one cylinder.

11. The apparatus as specified in claim 10 wherein said means for determining the elapsed time comprises timer means, means on the one cylinder for initiating said timer means at the initiation of the change in displacement of the one cylinder, and means for disabling said timer means associated with said other cylinder operable for disabling said timer means when the other cylinder moves a desired amount.

12. The apparatus of claim 11 wherein the one cylinder comprises the first cylinder.

13. The apparatus of claim 12 and an actuator operable to rotate the first cylinder in a first rotational direction from a rest position.

14. A method of determining the speed of propagation of a wave caused in a viscoelastic liquid when a surface of said liquid is placed in shear comprising the steps of:
   containing the liquid between two surfaces, said surfaces being independently movable relative to each other;
   suddenly changing displacement of one of the surfaces relative to the other surface by accelerating the one surface in a first direction relative to the other surface;
   sensing movement of the other of said surfaces caused by the wave propagated through said viscoelastic liquid at the time the propagated wave reaches said other surface; and
   determining an elapsed time which is a function of the time between the initiation of the displacement of said one surface and the resulting displacement of said other surface.

15. The method of claim 14 including the step of permitting the viscoelastic liquid and the surfaces to be in a state of rest before suddenly changing displacement of the first surface.

16. The method of claim 14 including the step of providing concentric circular cylinders nested to provide a substantially annular gap forming a chamber for containing the liquid.

17. The method of claim 16 wherein the step of suddenly changing displacement of one surface comprises initiating a rotational displacement.

* * * * *